United States Patent [19]

Izutsu et al.

[11] Patent Number: 4,650,666

[45] Date of Patent: Mar. 17, 1987

[54] PULLULAN AND SUGAR COATED PHARMACEUTICAL COMPOSITION

[75] Inventors: Yasuo Izutsu; Kiyomi Sogo, both of Osaka; Shizuo Okamoto, Amagasaki; Terukazu Tanaka, Osaka, all of Japan

[73] Assignee: Dainippon Pharmaceutical Co., Ltd., Japan

[21] Appl. No.: 673,480

[22] Filed: Nov. 20, 1984

[30] Foreign Application Priority Data

Nov. 30, 1983 [JP] Japan ................. 58-227334

[51] Int. Cl.⁴ ............................... A61K 9/34
[52] U.S. Cl. .................... 424/479; 514/777; 424/473
[58] Field of Search ............ 424/35; 514/777; 427/212

[56] References Cited

FOREIGN PATENT DOCUMENTS 49-62622  6/1974  Japan .................................. 424/35
51-101117  3/1975  Japan .................................. 424/35

OTHER PUBLICATIONS

Abstracts of 8th International Symposium on Carbohydrate Chemistry, p. 123, Aug. 16–20, 1976, Kyoto in Japan.

Abstracts of 8th Annual Meeting of the Society for Biomaterials in conjunction with the 14th International Biomaterials Symposium, p. 17, vol. V, Apr. 24–27, 1982, Florida in USA.

*Primary Examiner*—Stanley J. Friedman
*Assistant Examiner*—C. Joseph Faraci
*Attorney, Agent, or Firm*—Scully, Scott, Murphy & Presser

[57] ABSTRACT

Novel sugar-coated pharmaceutical composition such as tablets, pills, granules or the like, which contains pullulan in the sugar layer for the purpose of preventing brownish color change of the composition with lapse of time, and a method for preparing the composition.

3 Claims, No Drawings

PULLULAN AND SUGAR COATED PHARMACEUTICAL COMPOSITION

This invention relates to a novel sugar-coated pharmaceutical composition containing pullulan in the sugar layer, more particularly, to a sugar-coated pharmaceutical composition such as tablets, pills, granules or the like, which contains pullulan in the sugar layer for the purpose of preventing brownish color change of the composition with lapse of time, and a method for preparing the composition.

Pullulan (other name: 4,4,6-trigluco-polysaccharide) is a polysaccharide produced from a cultivated fungus of *Aureobasidium pullulans*, i.e. an α-glucan consisting mainly of maltotriose as repeating units linearly jointed through α-1,6-glycosidic linkages, as shown in the formula:

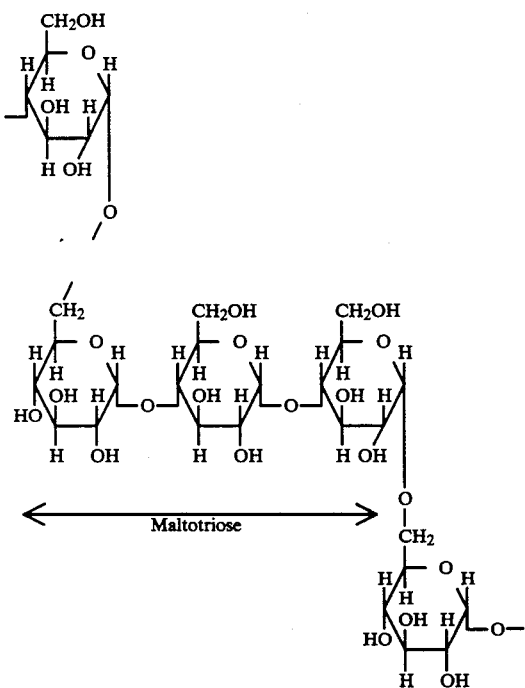

The pullulan is usually obtained in the form of an amorphous white powder and is non-toxic, odorless, edible but is non-digestible (cf. Abstracts of 8th International Symposium on Carbohydrate Chemistry, page 123, Aug. 16-20, 1976, Kyoto in Japan).

Pullulan is usually used in the fields of foodstuffs and adhesives, but is rarely used in pharmaceutical compositions. Application of pullulan to pharmaceutical composition is seen in the following literatures.

For instance, Japanese Patent Publication (unexamined) No. 12417/1978 (cf. Chemical abstracts, 88, 197668v) discloses a process for preparing a non-crystalline drug which comprises adding pullulan to an aqueous solution of a drug and then lyophilizing the aqueous solution, wherein the pullulan is used for the purpose of increase of solubility of the drug.

Abstracts of 8th ANNUAL MEETINGS OF THE SOCIETY FOR BIOMATERIALS in conjunction with the 14th INTERNATIONAL BIOMATERIALS SYMPOSIUM, page 17, Apr. 24-27, 1982, Florida in USA discloses as to "dissolution behavior of tablets for controlled-release of drug prepared from pullulan".

However, these literatures do not mention as to any sugar-coated pharmaceutical composition.

Japanese Patent Publication (unexamined) No. 101117/1976 (cf. Chemical Abstracts, 86, 34275j) discloses an enteric coating agent containing as an essential component an ester of pullulan with phthalic acid and/or obtained by incorporating pullulan in the sugar layer of the composition.

An object of this invention is to provide a novel sugar-coated pharmaceutical composition having no brownish color change with a lapse of time. Another object of the invention is to provide a method for sugar-coating of a solid composition with high manufacturing efficiency. These and other objects and advantages of the invention will be apparent to persons skilled in the art from the following description.

The sugar-coated pharmaceutical composition of this invention is prepared by coating a solid composition such as core tablets with a syrup containing pullulan in a conventional manner.

The syrup is prepared by dissolving pullulan as well as sugar in water optionally together with other conventional additives. Pullulan can easily be dissolved in water without producing undesirable agglomeration, and during the course of the syrup preparation, no air-bubble is formed. Other additives to be optionally incorporated into the syrup together with pullulan include lubricants (e.g. propylene oxide-ethylene oxide copolymer, or polyethylene glycol), suspending agents (e.g. talc, titanium dioxide, precipitated calcium carbonate, tribasic calcium phosphate) and the like. The syrup may also contain colorants as desired. The syrup containing pullulan can be used without filtering because no foreign substance is contained in succinic acid, but in this reference, pullulan is used in the form of an ester but not in the free form.

Sugar-coated solid compositions are usually prepared by sugar-coated the solid compositions with a syrup containing Arabia gum (i.e. Acacia gum), gelatin, or the like. When the solid composition is coated with a syrup containing gelatin or Arabia gum, brownish color change usually occurs with a lapse of time. In case of sugar-coated compositions having white or light colored coating, the brownish color change is particularly significant, which results in loss of product value and gives anxiety to patients who take the drugs.

It is disclosed in Japanese Patent Publication (unexamined) No. 108225/1974 (cf. Chemical Abstracts, 82, 103171d) that when tablets are prepared by sugar-coating with a syrup containing hydroxypropylcellulose (abbreviated as "HPC"), hydroxypropylmethylcellulose (abbreviated as "HPMC") and/or methylcellulose (abbreviated as "MC"), the tablets show neither the undesirable brownish color change nor cracking. Contrary to the disclosure, it is difficult to prepare such tablets, particularly the syrup, due to less solubility of HPC, HPMC or MC in the syrup.

The present inventors have intensively studied on an improved sugar-coated pharmaceutical composition having no brownish color change even if it is kept for a long period of time. As a result, it has been found that the desired sugar-coated pharmaceutical composition can be pullulan, unlike the syrups containing gelatin or Arabia gum.

Pullulan has usually various molecular weights in the range of about $1 \times 10^4$ to $2 \times 10^6$ depending on the processes for the production thereof. The pullulan suitable in the present invention has a molecular weight of about $5 \times 10^4$ to about $1 \times 10^6$, preferably about $7 \times 10^4$ to about $5 \times 10^5$, more preferably about $1 \times 10^5$ to about $3 \times 10^5$. The pullulan can be incorporated into the syrup in a wide range of concentration depending on the molecular weight thereof, but suitable concentration of pullulan is in the range of 0.1 to 17 w/w %, preferably 0.3 to 15 w/w %, particularly preferably 0.5 to 7 w/w %. When the concentration of pullulan is too high, the composition shows unfavorably less surface smoothness. Concentration of sugar in the syrup is not critical, but is usually in the range of 30 to 70 w/w %, preferably 35 to 65 w/w %.

Coating with the syrup containing pullulan can be carried out at any step in the conventional coating steps such as subcoating step, smoothing coating step and finishing coating step, but is preferably coated in the subcoating step. After the coating steps, the sugar-coated composition may optionally be treated with a polishing agents such a yellow wax or carnauba wax, as usual.

The thus-obtained sugar-coated pharmaceutical composition of this invention has the following advantages.

(1) Even under heating and/or lighting conditions, no brownish color changes occur unlike the tablets coated with a sugar syrup containing gelatin or Arabia gum (that is, it shows excellent aging stability).

(2) White or light-colored composition of this invention exhibits enhanced whiteness or brightness.

(3) It shows all properties required in sugar-coated pharmaceutical compositions, for instance, favorable anti-shock and disintegration properties.

The present invention is illustrated by the following Examples but should not be construed to be limited thereto.

EXAMPLE 1

Core tablets (100 mg/T) are repeatedly subjected to subcoating with the following syrup for subcoating until the tablet weight becomes 150 mg/T. The tablets thus subcoated are further subjected to finishing coating with simple syrup until the tablet weight becomes 160 mg/T and finally subjected to polishing treatment with carnauba wax to give clean white sugar-coated tablets.

| Syrup for subcoating | | |
|---|---|---|
| Sugar | | 42 w/w % |
| Pullulan* | | 2.1 w/w % |
| Talc | | 25 w/w % |
| Titanium dioxide | | 5 w/w % |
| Water | | q.s. |
| | Totally | 100 w/w % |

*Molecular weight: about 200,000

The white sugar-coated tablets were subjected to the following tests, wherein for the purpose of comparison, there were used reference tablets which were prepared in the same manner as described above except that Arabia gum (5.6 w/w %) was used instead of pullulan.

(1) Heat Resistance Test

Each tablet was stored in a sealed glass bottle at 50° C. for 30 days, and the Hunter's color difference ($\Delta E$), whiteness and yellow index of the tablets were measured by a color differences-photometer (Degital Color Computer CD-SCH-1, manufactured by Suga Test Machine Instruments Co., Ltd., Japan). The results are shown in the following Tables 1 to 3.

TABLE 1

Color difference of sugar-coated tablets stored at 50° C. in sealed glass bottle:

| Stored period (days) | Tablets of this invention (Pullulan) | Reference tablets (Arabia gum) |
|---|---|---|
| Initial | 0.0 | 0.0 |
| 10 | 0.6 | 3.4 |
| 15 | 0.6 | 4.2 |
| 30 | 0.7 | 6.3 |

The numerals in the table show Hunter's color difference ($\Delta E$).

TABLE 2

Whiteness of sugar-coated tablets stored at 50° C. in sealed glass bottle:

| Stored period (days) | Tablets of this invention (Pullulan) | Reference tablets (Arabia gum) |
|---|---|---|
| Initial | 97.2 | 93.4 |
| 10 | 97.0 | 90.8 |
| 15 | 96.9 | 90.1 |
| 30 | 96.9 | 88.0 |

The numerals in the table show whiteness (%).

TABLE 3

Yellow index of sugar-coated tablets stored at 50° C. in sealed glass bottle:

| Stored period (days) | Tablets of this invention (Pullulan) | Reference tablets (Arabia gum) |
|---|---|---|
| Initial | 0.5 | 4.0 |
| 10 | 1.5 | 9.7 |
| 15 | 1.7 | 11.2 |
| 30 | 1.9 | 14.3 |

The numerals in the table show yellow index.

(2) Heat Resistance Test

Each tablet was put in a drying chamber keeping at 40° C., 50° C. or 60° C. for 3 months, and the Hunter's color difference of the tablets was measured. The results are shown in Table 4.

TABLE 4

Color difference of sugar-coated tablets stored at 40 to 60° C. in drying chamber:

| Stored temperature (°C.) | Tablets of this invention (Pullulan) | Reference tablets (Arabia gum) |
|---|---|---|
| 40 | 2.0 | 5.2 |
| 50 | 2.0 | 10.5 |
| 60 | 3.4 | 13.8 |

The numerals in the table show Hunter's color difference ($\Delta E$).

(3) Light Resistance Test

Each tablet was put in an artificial illumination apparatus (light source: fluorescent lamp, illuminance: 6,000 lux), and the Hunter's color difference ($\Delta E$) of the tablets was measured. The results are shown in Table 5.

TABLE 5

Color difference of sugar-coated tablets exposed to light of a fluorescent lamp:

| Illumination time (hour) | Tablets of this invention (Pullulan) | Reference tablets (Arabia gum) |
|---|---|---|
| Initial | 0.0 | 0.0 |
| 50 | 0.5 | 1.7 |
| 100 | 0.6 | 2.3 |
| 200 | 1.0 | 4.1 |

The numerals in the table show Hunter's color difference ($\Delta E$).

EXAMPLE 2

Core tablets (180 mg/T) are repeatedly subjected to subcoating mutually with the following syrup for subcoating and a dusting powder until the tablet weight becomes 270 mg/T. The tablets thus subcoated are further subjected to smoothing coating with the following syrup for smoothing coating until the tablet weight becomes 300 mg/T. The tablets are further subjected to finishing coating with simple syrup until the tablet weight becomes 320 mg/T and finally subjected to polishing with carnauba wax to give clean white sugar-coated tablets.

| Syrup for subcoating | | |
|---|---|---|
| Sugar | 55 | w/w % |
| Pullulan* | 5 | w/w % |
| Water | 40 | w/w % |
| Totally | 100 | w/w % |
| Dusting powder for subcoating | | |
| Talc | 70 | w/w % |
| Sugar | 20 | w/w % |
| Corn starch | 10 | w/w % |
| Totally | 100 | w/w % |
| Syrup for smoothing coating | | |
| Sugar | 42 | w/w % |
| Pullulan* | 2.1 | w/w % |
| Talc | 25 | w/w % |
| Titanium dioxide | 5 | w/w % |
| Water | 25.9 | w/w % |
| Totally | 100 | w/w % |

*Molecular weight: about 200,000

EXAMPLE 3

In the same manner as described in Example 2 except that core tablets (100 mg/T) are coated with the following coating materials, there are obtained clean white sugar-coated tablets (160 mg/T).

| Syrup for subcoating | | |
|---|---|---|
| Sugar | 35 | w/w % |
| Pullulan* | 15 | w/w % |
| Water | 50 | w/w % |
| Totally | 100 | w/w % |
| Dusting powder for subcoating | | |
| Talc | 50 | w/w % |
| Sugar | 20 | w/w % |
| Titanium dioxide | 10 | w/w % |
| Corn starch | 10 | w/w % |
| Tribasic calcium phosphate | 10 | w/w % |
| Totally | 100 | w/w % |
| Syrup for smoothing coating | | |
| Sugar | 42 | w/w % |
| Pullulan* | 2.1 | w/w % |
| Talc | 25 | w/w % |
| Titanium dioxide | 5 | w/w % |
| Water | 25.9 | w/w % |
| Totally | 100 | w/w % |

*Molecular weight: about 200,000

EXAMPLE 4

In the same manner as described in Example 1 except that core tablets (260 mg/T) are coated with the following subcoating material, there are obtained clean white sugar-coated tablets (400 mg/T).

| Syrup for subcoating | | |
|---|---|---|
| Sugar | 50.4 | w/w % |
| Pullulan* | 2.4 | w/w % |
| Tribasic calcium phosphate | 10 | w/w % |
| Talc | 5 | w/w % |
| Titanium dioxide | 5 | w/w % |
| Water | 27.2 | w/w % |
| Totally | 100 | w/w % |

*Molecular weight: about 100,000

EXAMPLE 5

In the same manner as described in Example 1 except that core tablets (100 mg/T) are coated with the following subcoating material, there are obtained clean white sugar-coated tablets (160 mg/T).

| Syrup for subcoating | | |
|---|---|---|
| Sugar | 42.7 | w/w % |
| Pullulan* | 0.5 | w/w % |
| Precipitated calcium phosphate | 25 | w/w % |
| Titanium dioxide | 5 | w/w % |
| Water | 26.8 | w/w % |
| Totally | 100 | w/w % |

*Molecular weight: about 300,000

EXAMPLE 6

Core tablets (120 mg/T) containing levomepromazine maleate are repeatedly subjected to subcoating with the following syrup for subcoating until the tablet weight becomes 190 mg/T. The tablets thus subcoated are further subjected to finishing coating with the following syrup for finishing coating until the tablet weight becomes 200 mg/T and finally subjected to polishing with carnauba wax to give clean white sugar-coated tablets.

| Syrup for subcoating | | |
|---|---|---|
| Sugar | 42 | w/w % |
| Pullulan* | 2.1 | w/w % |
| Talc | 25 | w/w % |
| Titanium dioxide | 5 | w/w % |
| Water | 25.9 | w/w % |
| Totally | 100 | w/w % |
| Syrup for finishing coating | | |
| Sugar | 66 | w/w % |
| Pullulan* | 0.1 | w/w % |
| Water | 33.9 | w/w % |
| Totally | 100 | w/w % |

*Molecular weight: about 200,000

What is claimed is:

1. In a sugar-coated pharmaceutical composition comprising a core containing an active medicament and a sugar-coating layer, the improvement which comprises having a pullulan incorporated in the sugar-coating layer said pullulan having a molecular weight of about $5 \times 10^4$ to about $1 \times 10^6$.

2. The composition according to claim 1, wherein the pullulan has a molecular weight of about $1 \times 10^5$ to about $3 \times 10^5$.

3. The composition according to claim 1, which is in the form of a tablet.

* * * * *